United States Patent [19]

Peltzman

[11] 4,153,806

[45] May 8, 1979

[54] RECOVERY OF VICINAL GLYCOL ESTERS BY PLURAL STAGE DISTILLATION

[75] Inventor: Alan Peltzman, Jamaica, N.Y.

[73] Assignee: Halcon Research and Development Corp., New York, N.Y.

[21] Appl. No.: 841,082

[22] Filed: Oct. 11, 1977

[51] Int. Cl.² .................................... C07C 67/06
[52] U.S. Cl. .................... 560/246; 203/81; 203/88; 203/DIG. 19
[58] Field of Search ............... 560/248, 243, 247, 246; 203/74, 81, 88, DIG. 19

[56] References Cited

U.S. PATENT DOCUMENTS

| | | | |
|---|---|---|---|
| 3,140,243 | 7/1964 | Feder et al. | 203/81 |
| 3,719,722 | 3/1973 | Tschopp | 203/81 |
| 3,772,156 | 11/1973 | Johnson et al. | 203/81 |
| 3,859,368 | 1/1975 | Kollar | 203/81 |
| 3,907,874 | 9/1975 | Harvey et al. | 560/247 |

Primary Examiner—Wilbur L. Bascomb, Jr.
Attorney, Agent, or Firm—William C. Long; David Dick; Jack B. Murray, Jr.

[57] ABSTRACT

Ethylene glycol esters or propylene glycol esters are recovered from their mixtures with high- and low-boiling organo-halogens by (1) distilling the mixture in a first distillation zone to form a first bottoms stream comprising the high-boiling organo-halogen impurities and a first overhead stream comprising the ethylene glycol esters or propylene glycol esters together with the low-boiling organo-halogen impurities, and (2) distilling at least a portion of the first overhead stream in a second distillation zone to form a second overhead stream containing the low-boiling organo-halogen impurities and a second bottoms stream comprising the desired ethylene glycol esters or propylene glycol esters having a substantially reduced concentration of the organo-halogen impurities.

16 Claims, 4 Drawing Figures

RECOVERY OF VICINAL GLYCOL ESTERS BY PLURAL STAGE DISTILLATION

BACKGROUND OF THE INVENTION

1. Field of the Invention

This invention relates to the recovery of vicinal glycol esters from mixtures containing the same, and more specifically to recovery of ethylene glycol esters or propylene glycol esters from mixtures with high- and low-boiling organo-halogen impurities.

2. Description of the Prior Art

Ethylene glycol and 1,2-propylene glycol (hereinafter referred to as propylene glycol) are chemicals of acknowledged commercial importance. Ethylene glycol is used, for example, in the preparation of antifreeze compositions and in the manufacture of polyester fibers. Ethylene glycol manufacturing processes of commercial interest have generally been based upon ethylene oxide as a raw material. Recently, however, processes have been developed which make it possible to produce ethylene glycol and propylene glycol without the necessity for the intermediate manufacture of the epoxide. These processes employ the liquid phase reaction of the olefin, a carboxylic acid and molecular oxygen, in the presence of catalysts. For example, U.S. Pat. No. 3,770,813 employs a conjoint catalyst system involving specific metals (or organic bases) in conjunction with iodine. Other processes such as those of U.S. Pat. Nos. 3,689,535 and Canadian Pat. No. 888,749 employ certain variable valent cations together with chlorine or bromine (or their compounds) as catalysts. Yet other processes employ noble-metal based systems and alkali metal halides in conjunction with redox systems (see U.S. Pat. No. 3,262,969). These processes, however, result in the production of by-products in addition to the desired vicinal glycol ester products, and these by-products include organo-halogen compounds as well as ester precursors.

The presence of more than minor amounts of such organo-halogen compound impurities in the vicinal glycol products can frequently interfere with their utilization. For example, it is known that in the case of ethylene glycol diacetate, the presence of more than 100 to 200 ppm of organo-halogen compounds in this material interferes with its pyrolysis to form vinyl acetate (see U.S. Pat. No. 3,804,887). Where it is desired to hydrolyze such esters to produce ethylene glycol or propylene glycol, the presence of organo-halogen compound impurities unfavorably affects the hydrolysis since the halogen compounds have a tendency to contaminate the glycol, and their presence introduces corrosion problems, often necessitating employment of more expensive materials of construction than would otherwise be required.

While it is possible to efficiently remove substantially all of the organo-halogen compound impurities by contacting the impure esters containing these impurities with compounds of selected metals, (see, U.S. Pat. No. 3,884,965), it would be advantageous to recover the desired esters by distillation and recycle the separated by-products and unreacted starting materials.

SUMMARY OF THE INVENTION

It has now been found that vicinal glycol esters can be efficiently recovered from their mixtures with high- and low-boiling organo-halogens by (1) distilling the mixture in a first distillation zone to form a first bottoms stream comprising the high-boiling organo-halogen impurities and a first overhead stream comprising the ethylene glycol esters or propylene glycol esters together with the low-boiling organo-halogen impurities and (2) distilling at least a portion of the first overhead stream in a second distillation zone to form a second overhead stream containing the low-boiling organo-halogen impurities and a second bottoms stream comprising the desired ethylene glycol esters or propylene glycol esters having a substantially reduced concentration of the organo-halogen impurities. In accordance with the invention, concentrations of the organo-halogen impurities in the second bottoms stream of on the order of 10 to 20 ppm (calculated as halide), and lower, can be obtained, if desired. For some uses of the vicinal glycol esters, however, it is sufficient to reduce the concentration of these organo-halogen compound impurities to less than 1000 to 2000 ppm, and preferably less than 100 to 200 ppm, calculated as the halide, and these concentrations can be readily achieved by this process.

It has been surprisingly discovered that the above distillative sequence in which the high-boiling organo-halogen impurities are removed as bottoms in a first distillation step and in which the low-boiling organo-halogen impurities are removed as overhead in a second distillation, is critical to allow distillative recovery of vicinal glycol esters having substantially reduced concentrations of organo-halogen impurities. A reversed distillative sequence, in which the low-boiling organo-halogens are recovered as overhead in a first distillation followed by a second distillation of the resulting bottoms for recovery of the vicinal glycol esters as overhead, has been surprisingly found to result in the formation of significant additional low-boiling organo-halogens in the second distillation, thereby contaminating the ester overhead and making impossible the recovery of the desired vicinal glycol esters having a reduced concentration of organo-halogen impurities.

DETAILED DESCRIPTION OF THE INVENTION

As indicated above, the recovery of vicinal glycol esters from their liquid mixtures with organo-halogen compound impurities is highly desirable since most uses of such esters cannot tolerate substantial levels of such halogen impurities. In developing a distillative method for recovering these esters, it was unexpectedly discovered that a distillative sequence in which low-boiling organo-halogens are removed as overhead product in a first distillation zone and in which the resulting bottoms is distilled in a second distillation zone to recover the desired esters as a second overhead product, results in an ester overhead product which contains unacceptably large amounts of low-boiling organo-halogens. Moreover, increasing the reflux and number of theoretical vapor/liquid contacting stages in such a distillation did not produce a significant decrease in the concentration of such low-boiling impurities in the ester overhead product. It was then surprisingly found that the source of this ester overhead contamination problem resided in the rapid formation in the second distillation of large amounts of low-boiling organo-halogens from the high-boiling organo-halogens. While it is not desired this invention be limited by any theory, it is believed the high-boiling organo-halogens react with the desired vicinal glycol esters to form the low-boiling organo-halogens and other derivatives of the glycol esters. These reactions may be exemplified by the reaction of ethylene glycol acetates with diethylene glycol bromo acetate and diethylene glycol dibromide, to yield diethylene glycol acetate and low-boiling organo-halogens as illustrated in equations (1) and (2):

The present invention solves the above problems and allows recovery of vicinal glycol esters substantially free of organo-halogen compound impurities from impure mixtures containing the same together with the organo-halogen compound impurities.

DEFINITIONS

For a more complete understanding of the present invention, terms employed in this application are defined below.

The term "oxygen-based olefin-oxidation process" as used herein refers to any process in which molecular oxygen, carboxylic acid and olefin are reacted in the presence of metallic catalyst and halogen-containing compounds to form vicinal glycol esters (e.g., in accordance with any of the processes described in U.S. Pat. Nos. 3,770,813, 3,689,535, 3,262,967, and 3,907,874; Canadian Pat. No. 888,749, and Japanese patent application No. 58803/66, published May 25, 1970, which are hereby incorporated by reference), it being understood that such a process includes the use of air as the oxygen source.

The term "vicinal glycol esters" as used herein refers to esters of vicinal glycols having 2 or 3 carbon atoms in the glycol moiety (e.g., an ester of 1,2-ethanediol) and having an acyloxy moiety derived from a 1 to 5 carbon atom aliphatic hydrocarbon monobasic carboxylic acid. The esters contemplated are therefore the formates, acetates, propionates, butyrates, isobutyrates or valerates of ethylene glycol or propylene glycol as well as mixtures of such. The term as herein used encompasses the diester as well as the monoester and also includes mixed esters such as, for example, 2-acetoxy-1-formoxyethane. The presence of free (i.e., not esterified) glycol has no effect on the process of this invention and some quantity thereof (up to about 20% mole basis) can often be present; such free glycol is for convenience included with the scope of the term here defined.

By way of illustration, when dealing with acetic acid esters of ethylene glycol, the vicinal glycol esters recovered by the process of this invention consists essentially of ethylene glycol diacetate (i.e., 1,2-diacetoxyethane), ethylene glycol monoacetate and ethylene glycol itself. Similarly, when dealing with acetates of propylene glycol, the glycol esters recovered by the process of this invention include propylene glycol diacetate (1,2-diacetoxypropane), the propylene glycol mono-esters (both 1-acetoxypropan-2-ol and 2-acetoxypropan-1-ol) and 1,2-propylene glycol itself. When dealing with vicinal glycol esters of two or more carboxylic acids, mixed esters are also present. For example, 2-acetoxy-1-formoxyethane can be present in addition to ethylene glycol diacetate, ethylene glycol mono-acetate, ethylene glycol diformate, ethylene glycol mono-formate, and ethylene glycol itself when dealing with mixed acetic acid and formic acid esters of ethylene glycol.

The term "organo-halogen impurities" as used herein is intended to refer to halogen-containing organic compounds selected from the group consisting of compounds of the formula:

wherein: X is chlorine, bromine or iodine; Q and Q' are radicals independently selected from the group consisting of chlorine, bromine, iodine, hydroxy and $C_1$–$C_5$ alkanoyloxy (i.e., where R is hydrogen or $C_1$–$C_4$ alkyl); $R_1$, $R_2$, $R_3$ and $R_6$ are independently selected from the group consisting of hydrogen and methyl; and $R_4$ and $R_5$ are independently selected from the group consisting of hydrogen, methyl and Q', wherein Q' is as defined above; with the provisos that the total number of carbon atoms of $R_1$ plus $R_2$ is either zero or one, the total number of carbon atoms of $R_3$ through $R_6$ inclusive is an integer from zero to two (i.e., zero, one or two), $R_3$ and $R_4$ are not both methyl, and $R_5$ and $R_6$ are not both methyl; and mixtures thereof.

Generally, more than 70 mole percent of the organic halogen will be in one or more of the above forms and often as much as 90 mole percent or even more of the total organo-halogen compound will be present in one or more forms. The precise nature of these impurities and their relative proportions to one another, of course, depend upon the reactants used for production of the ester feed. Their nature will also depend upon the catalyst system employed in the manufacture of the ester feed to this process and particularly upon the nature of the halogen component of the catalyst system and used (i.e., whether a chlorine, bromine or iodine catalyst component is employed). For example, when the ester feed is derived from the reaction of ethylene, acetic acid and oxygen and when the system used to catalyze the reaction comprises bromine, the organo-halogen compound impurities would include brominated analogues of ethylene glycol and its esters and of diethylene glycol and its esters, including such materials as ethylene dibromide (1,2-dibromoethane), ethylene bromohydrin (1-bromoethan-2-ol), bromoethyl acetate (1-acetoxy-2-bromoethane), diethylene glycol dibromide (2,2'-dibromo-diethylether),2-bromo-2'-hydroxy-diethyl ether, 2-bromo-2'-acetoxydiethyl ether, ethylene glycol acetate bromoacetate and diethylene glycol acetate bromoacetate. In addition, the formate analogues of the acetoxy compounds identified in the preceding sentence would also be present, albeit in lesser quantities. The formate moieties would be formed by oxidative attack upon either or both the ethylene or acetic acid reactants causing carbon-carbon scission thereof. Also, such formate analogues of the foregoing acetoxy compounds may result from use of formic acid in addition to acetic acid in the olefin oxidation reaction in accordance with Belgian Pat. No. 823,225. When propylene and acetic acid are respectively the olefin and carboxylic acid reactants, the organo-halogen compound impurities would include brominated analogues of propylene glycol and of dipropylene glycol such as 1,2-dibromopropane; 1-bromopropan-2-ol; 2-bromopropan-1-ol; 1-bromo-2-acetoxypropane; 2-bromo-1-acetoxypropane; 1,1'dibromo di-n-propyl ether; 2,2'-dibromo di-n-propyl ether; 1,2'-dibromo-di-n-propyl ether; 1-bromo-1'-acetoxy-diisopropyl ether; 2-bromo-1'-acetoxy-diisopropyl ether; 1-acetoxy-isopropyl-2'-bromo-n-propyl ether, among others. When dealing with mixed ethylene and propylene olefin reactants and again using acetic acid as illustrative, mixtures of all of the foregoing will be present, together with corresponding analogues of ethyl propyl ether such as, typically, 2-bromoethyl-1-bromopropyl ether. When higher homologues of acetic acid such as butyric acid are used as reactants in preparation of the ester feed, the halogenated impurities would include not only the carboxylate esters corresponding to the higher acid (e.g., the butyrates) but would also include lower homologues of such carboxylates, again resulting from carbon-carbon scission, including the acetate and formate.

With different catalyst systems such as, for example, one comprising chlorine in conjunction with a noble metal or a variable valent cation (such as those disclosed in U.S. Pat. No. 3,681,535 and Canadian Pat. No. 888,749), the chlorine analogues of any one or more of the foregoing would be organo-halogen compound impurities encountered and, similarly, when iodine is the halogen employed, the corresponding organo-iodine compounds would be encountered. Of the foregoing (again referring, for convenience, to ethylene, acetic acid and bromine), those most likely to be prevalent in the organo-halogen compound impurity component of the feed to the process of this invention are bromoethyl acetate and diethylene glycol dibromide (i.e., 1-acetoxy-2-bromoethane and 2,2'-dibromodiethyl ether, respectively).

The "impure vicinal glycol ester liquid" which is treated by the process of the present invention can also contain ester precursors and non-halogenated by-products, as when the impure ester liquid is obtained as product using an oxygen-based olefin-oxidation process. As used herein, the term "ester precursors" is intended to refer to unreacted starting materials used in the formation of the ester, i.e., carboxylic acid (e.g., acetic and/or formic acid) and olefin (e.g., ethylene or propylene). This term also is defined to include catalyst (e.g., a catalyst such as palladium, tellurium or selenium), which may include both volatile and non-volatile catalyst components. The term "ester precursor" is also defined to include, dissolved gases such as oxygen and inert gases, e.g., argon and nitrogen (which may be present as a result of the use of air as the source of the oxygen-containing gas, or may be present as an inert diluent if a higher oxygen content gas is employed as the oxygen source).

The term "non-halogenated by-product" as used herein is intended to refer to non-halogenated by-products formed in the oxygen-based olefin-oxidation process and includes compounds such as ether derivatives of the desired vicinal glycol esters; aldehydes (e.g., acetaldehyde and formaldehyde); glycolic acids; various ring compounds such as dioxane and 1,3-dioxolane; dissolved gases, such as carbon dioxide and carbon monoxide and water. Examples of ether derivatives of the vicinal glycol esters, when dealing with acetic acid esters of ethylene glycol, include diethylene glycol diacetate, diethylene glycol monoacetate, triethylene glycol diacetate, triethylene glycol monoacetate, and ether alcohols such as diethylene glycol and triethylene glycol. The impure ester liquid can also contain alkoxylated ester derivatives such as, for example, ethylene glycol acetate acetoxyacetate [H$_3$C(O)COCH$_2$CH$_2$OC(O)CH$_2$OC(O)CH$_3$],and diethylene glycol acetate acetoxy acetate when dealing with acetic acid esters of ethylene glycol, and such alkoxylated ester derivatives are included within the term "non-halogenated by-products" as defined herein.

Of course, it will be understood that some overlap in the above-defined terms may occur. For example, the same compound can be both an ester precursor and a non-halogenated or halogenated by-product. Thus, carbon dioxide can be both a reaction by-product (as when formed in the oxidation step) and an ester precursor (e.g., if passed to the oxidation step as component of the oxygen-containing gas). Likewise, halogenated compounds which are recovered from the impure ester liquid and recycled to the oxidation reactor can be viewed as both ester precursors (since additional ester can be expected to be formed therefrom on recycle to oxidation) and as halogenated by-products. However, for the purposes of this invention, the compounds are defined as set forth above and such overlap as may exist facilitates a description of the invention but is not material either to an understanding of, or to the practice of, this invention.

Organo-halogen compound impurities having a normal boiling point (i.e., at atmospheric pressure) greater than the desired vicinal glycol esters are referred to herein as the "high-boiling organo-halogens", and organo-halogen compound impurities having a normal boiling point lower than the desired vicinal glycol esters are referred to herein as the "low-boiling organo-halogens." Likewise, non-halogenated by-products having normal boiling points above the vicinal glycol esters are referred to as the "high-boiling non-halogens," and the term "low-boiling non-halogens" is hereinafter intended to refer to non-halogenated by-products having low normal boiling points than the desired vicinal glycol esters. In the case of vicinal glycol esters of ethylene produced by an oxygen-based olefin-oxidation process using a bromide-containing compound as component of the catalyst medium, the high-boiling organo-halogens present in the impure vicinal glycol ester liquid treated by the present invention can be exemplified by such compounds as diethylene glycol bromoacetate, diethylene glycol bromo formate, diethylene glycol bromohydrin, ethylene glycol acetate bromoacetate, ethylene glycol formate bromoformate, diethylene glycol acetate bromoacetate, diethylene glycol formate bromoformate; diethylene glycol dibromide, and the low-boiling organo-halogens can be exemplified by such compounds as vinyl bromide, hydrogen bromide, ethylene dibromide, ethylene glycol bromo acetate, ethylene bromohydrin, ethylene glycol bromoformate, and the like. Similarly, the high-boiling non-halogens in such impure vicinal glycol ester liquid can be exemplified by diethylene glycol diacetate, diethylene glycol diformate, diethylene glycol monoacetate, diethylene glycol monoformate, diethylene glycol, glycolic acid and trimeric and detrameric derivatives of the foregoing, and the like. The low-boiling non-halogens can be exemplified by such compounds as 1,3-dioxolane, dioxane, ethyl acetate, water, acetic acid, formic acid, methyl acetate, methanol, acetaldehyde, formaldehyde, CO, $CO_2$ and the like.

PROCESS DESCRIPTION

The source of the impure vicinal glycol ester liquid treated by the process of this invention is not critical, although the process is particularly useful for recovering vicinal glycol esters form impure ester liquids produced for an oxygen-based olefin-oxidation process. The precise composition of the impure vicinal glycol ester liquid will therefore vary widely depending upon the particular source of the feed, and is not critical to the present invention. However, the impure ester feed will generally comprise from about 10 to 80 weight percent, usually from about 15 to 70 weight percent, vicinal glycol esters (e.g., ethylene glycol monoacetate, ethylene glycol diacetate and the like); and from about 0.1 to 30 weight percent, usually from about 10 to 20 weight percent, organo-halogen impurities. These will comprise generally up to about 30 weight percent, usually from about 10 to 20 weight percent, high-boiling organo-halogens, and generally up to about 70 weight percent, usually from about 20 to 50 weight percent, low-boiling organo-halogens. In addition, as where the impure vicinal glycol ester liquid to be treated is produced by an oxygen-based olefin-oxidation process, the impure ester liquid can also contain up to about 60 weight percent, usually from about 5 to 50 weight percent, carboxylic acid; up to about 10 weight percent, usually from about 0.01 to 5 weight percent, catalyst; up to about 5 weight percent, usually from about 0.01 to 1 weight percent, other ester precursors; up to about 10 weight percent, usually from about 0.2 to 8 weight percent, water; and from about 5 to 20 weight percent, usually from about 8 to 16 weight percent, other non-halogenated by-products (on a water-free basis), which will comprise generally up to about 70 weight percent, usually up to about 60 weight percent, high-boiling non-halogens and generally up to about 30 weight percent, usually up to about 40 weight percent, low-boiling non-halogens.

It will be appreciated that the process of the present invention allows recovery of vicinal glycol esters from complex mixtures containing the desired vicinal glycol esters together with organo-halogen compounds and ester precursor. It will also be appreciated that the complexities in recovering the esters are multiplied by the fact that the organo-halogen compounds and ester precursors include both higher- and lower-boiling compounds than the desired esters.

In one embodiment, the process of the present invention comprises a two-step process in which impure vicinal glycol ester liquid containing high-boiling and low-boiling organo-halogens, in addition to the desired vicinal glycol esters, is passed to a first distillation zone for recovery of vicinal glycol esters and low-boiling organo-halogens as a first overhead product and separation of high-boiling organo-halogens as a first bottoms product. The overhead product is then distilled in a second distillation zone for recovery of a second bottoms product comprising the vicinal glycol esters substantially free of organo-halogen compound impurities and separation of low-boiling organo-halogens as a second overhead product.

In accordance with a second embodiment, as where the impure vicinal glycol ester liquid (in addition to the vicinal glycol esters and high-and low-boiling organo-halogens) contains ester precursors (e.g., catalyst, carboxylic acid and water) and non-halogenated by-products, the impure vicinal glycol ester liquid can be first distilled to separate the non-volatiles (e.g., catalyst) as bottoms, and the overhead obtained, comprising carboxylic acid, water, vicinal glycol ester and halogenated and non-halogenated by-products, can be distilled to separate carboxylic acid and water as overhead and to recover as bottoms product a crude ester mixture containing vicinal glycol esters, organo-halogen impurities and non-halogenated by-products. The crude ester mixture so produced can then be passed to the successive distillations described above with respect to the first embodiment, i.e., the crude ester mixture can be distilled to form an overhead product containing low-boiling organo-halogens, low-boiling non-halogenated by-products and vicinal glycol esters, which can then be subjected to a further distillation for recovery of bottoms product comprising the desired vicinal glycol esters substantially free of organo-halogens, ester precursors and non-halogenated by-products. Optionally, as when the impure vicinal glycol ester liquid contains substantial amounts of fixed gases (e.g., $O_2$, $N_2$, etc.), the impure ester liquid may be first flashed in a flash zone to remove fixed gases as overhead and the flashed liquid then treated in accordance with the embodiment described above.

Figure 1:
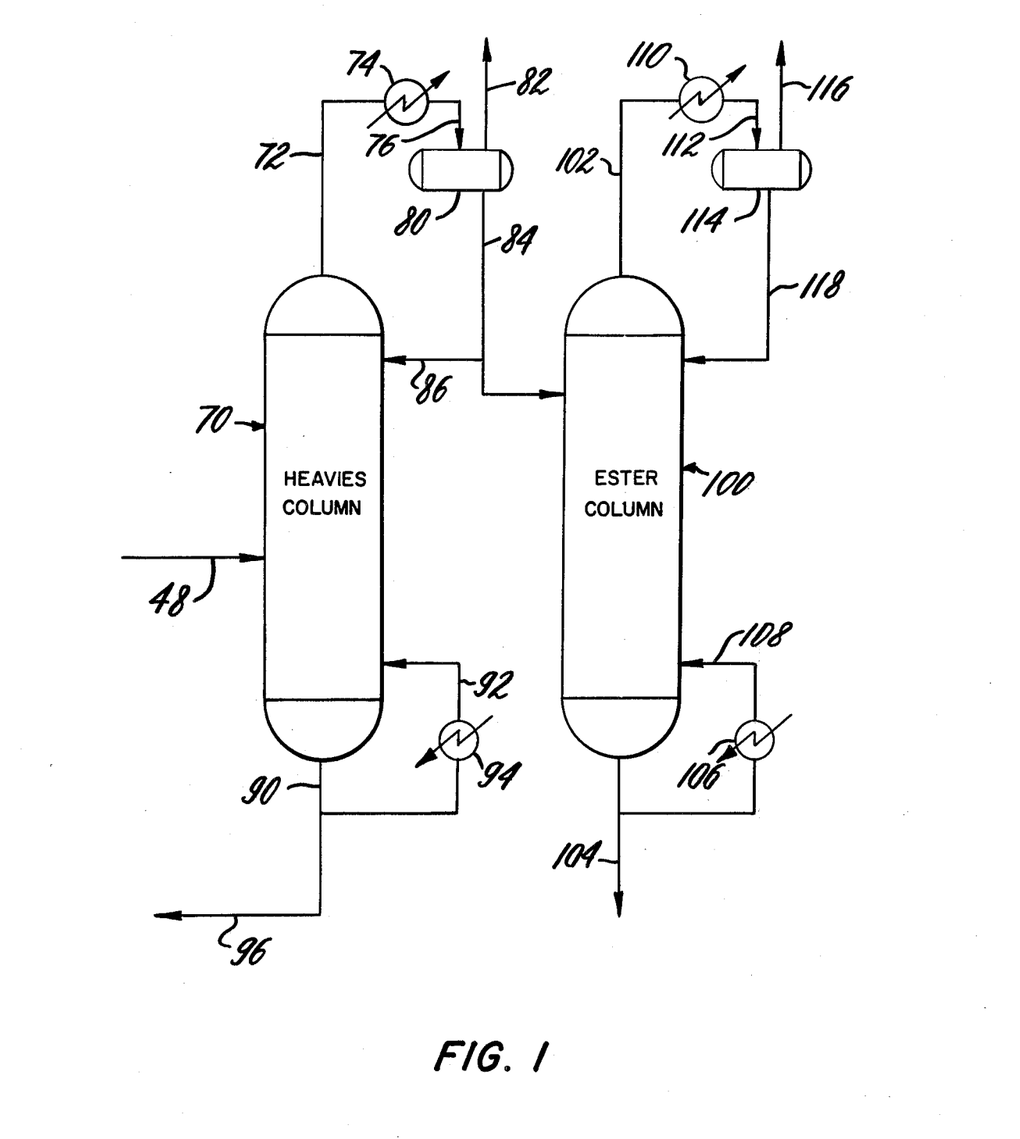
FIG. 1 is a diagrammatic illustration of one embodiment of the process of the present invention.
Figure 2:
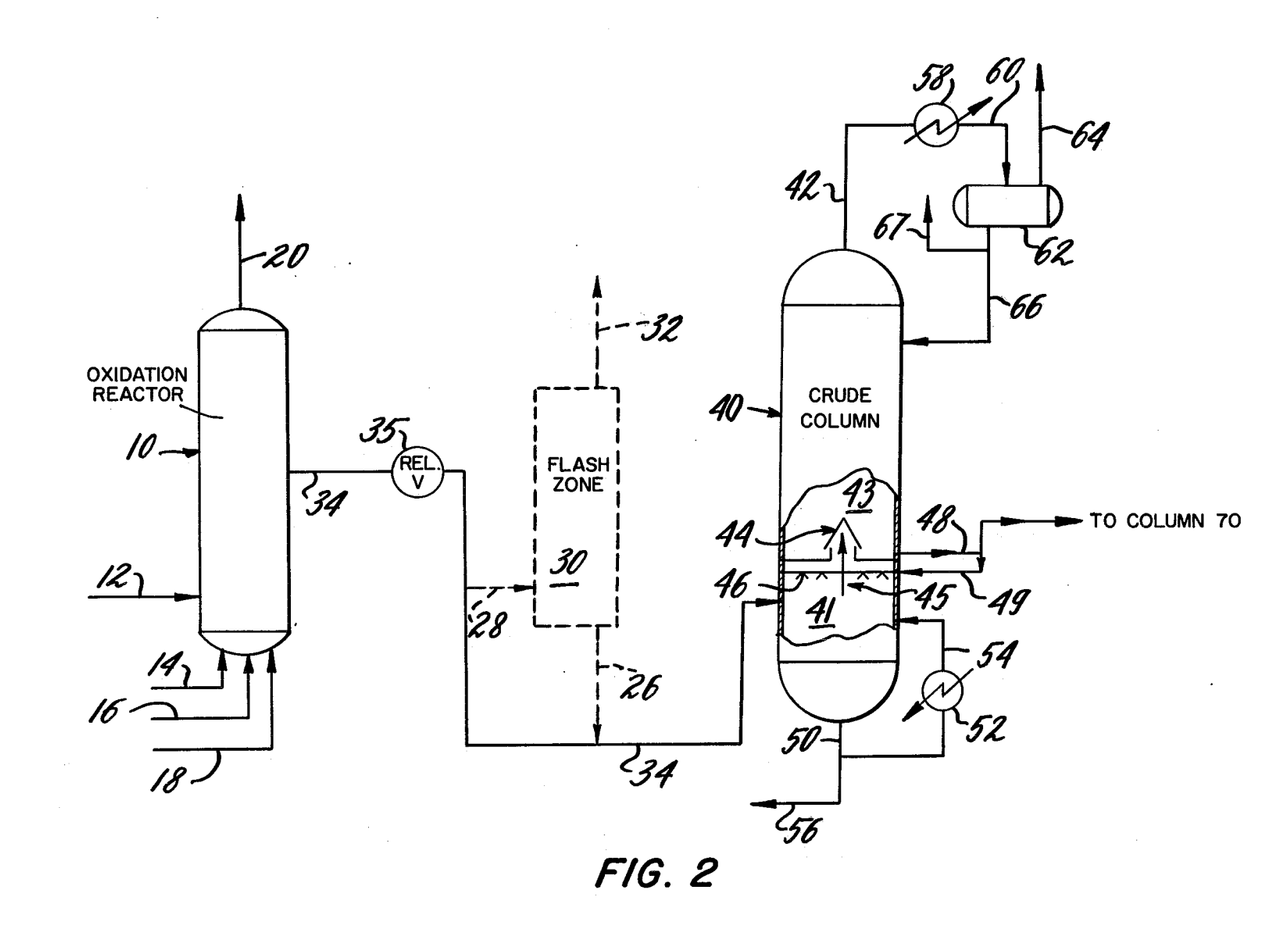
FIG. 2 is a diagrammatic illustration of a second embodiment of the process of the present invention.

The annexed drawings schematically depict apparatus for the conduct of the process of this invention and are presented to further illustrate and describe the manner of conducting this process. Thus, FIG. 1 is a diagrammatic illustration of one embodiment of the process of the present invention, and FIG. 2 is a diagrammatic illustration of a second embodiment of the process of the present invention. For ease and simplicity in the following discussion, but without intending thereby to imply any limitation upon the scope of this invention, the arrangement of the schematically depicted apparatus and the following description thereof presuppose continuous operation of the process of this invention and further presuppose that the totality of the ester feed is treated in accordance therewith, although the invention is not so limited.

Referring now to the drawings, wherein like numerals refer to the same or similar element, there is illustrated in FIG. 1 the recovery of vicinal glycol esters in accordance with one embodiment of the present invention from an impure vicinal glycol ester liquid comprising, e.g., from about 10 to 80 weight percent vicinal glycol esters and from about 0.1 to 30 weight percent organo-halogen compound impurities.

In heavies column 70 the impure ester liquid, passed thereto via conduit 48, is contacted with downwardly flowing reflux liquid (introduced to the upper portion of column 70 via conduit 86) and upwardly flowing vapors, resulting from the introduction to the lower portion of column 70 of heated fluid via conduit 92. Liquids collecting in the lower portion of column 70 are withdrawn therefrom as a first bottoms product via conduit 90 and will generally contain up to about 90 percent and more of the high-boiling organo-halogens contained in the impure ester liquid introduced to column 70. A portion of the first bottoms product is recycled to heavies column 70 via reboiler 94 and conduit 92 to provide the heat necessary for operation of column 70. Vapors are withdrawn from the upper portion of column 70 via conduit 72 and are passed to a condenser 74, which may be either a partial or (as is preferred) a total condenser, and the effluent therefrom passed via conduit 76 to separator 80. In the event a partial condenser is used, uncondensed vapors are withdrawn from separator 80 via conduit 82. A portion of the condensate withdrawn from separator 80 via conduit 84 is passed via conduit 86 as liquid reflux to heavies column 70.

The portion of withdrawn condensate which is passed as liquid reflux to heavies column 70 can vary widely but is generally sufficient to provide a minimum liquid reflux ratio for column 70 of from about 0.01:1 to 10:1, usually from about 0.5:1 to 5:1.

The remaining portion of the condensate withdrawn via conduit 84 comprises the first overhead product and is passed as feed to the upper portion of second distillation column 100 (i.e., the "ester column"). This stream generally contains at least about 90 percent of the vicinal esters contained in the impure ester liquid passed to heavies column 70. Preferably, the first overhead product passed to column 100 contains not greater than about 1.0 percent, and more preferably not greater than about 0.5 percent, of the high-boiling organo-halogens passed to heavies column 70 via conduit 48.

Heavies column 70 can be operated under wide ranges of temperature and pressure, with the precise temperature and pressure selected for use depending on such factors as the composition of the impure ester liquid passed thereto, the degree of separation of organo-halogen impurities desired, and other factors. Generally, however, heavies column 70 will be operated at a bottoms temperature of from about 150° to 300° C., preferably from about 210° to 250° C., and at a pressure of from about 500 to 5000 mm Hg, preferably from about 1200 to 1400 mm Hg. However, higher or lower temperatures and pressures can be employed. The number of theoretical vapor/liquid contacting stages employed in heavies column 70 can also vary widely, but will generally range from about 5 to 15 minimum theoretical stages, preferably from about 9 to 13 minimum theoretical stages, above the impure ester liquid feed thereto and from about 1 to 10 minimum theoretical stages, preferably from about 3 to 7 minimum theoretical stages, below the impure ester liquid feed thereto.

The overhead product passed as feed to ester column 100 is contacted therein with upwardly flowing vapor (resulting from the introduction to the lower portion of column 100 of heated fluid via conduit 108) and downwardly flowing liquid (introduced to the upper portion of column 100 via conduit 118). Liquids collecting in the lower portion of zone 100 comprise the second bottoms product and contain the desired vicinal glycol esters having substantially reduced concentration of organo-halogen impurities.

The liquid vicinal glycol esters are withdrawn as product via conduit 104, with a portion of the bottoms being recycled to column 100 via reboiler 106 and conduit 108 to provide the heat necessary for operation of column 100. Vapor is withdrawn from the upper portion of column 100 via conduit 102 and passed to condenser 110, which may comprise either a partial or total condenser. The effluent from condenser 110 is passed via conduit 112 to separator 114. In the embodiment illustrated in FIG. 1, condenser 110 is a partial condenser, and uncondensed vapors comprising low-boiling organo-halogens are withdrawn via conduit 116. Condensate is passed from separator 114 via conduit 118 as liquid reflux to the upper portion of ester column 100.

The conditions of temperature and pressure employed in ester column 100 can vary widely and will, of course, depend on the precise composition of the liquid introduced via conduit 84 as feed to the column, the degree of separation of impurities from the vicinal glycol esters desired and other factors, and may be readily ascertained by the skilled practitioner. Generally, however, ester column 100 is operated at a bottoms temperature of from about 150° to 300° C., preferably from about 200° to 240° C., and a bottoms pressure of from about 500 to 5000 mm Hg, preferably from about 2000 to 2800 mm Hg. Generally, the minimum reflux ratio for column 100 is from about 0.1:1 to 10:1, and preferably from about 1:1 to 4:1.

The number of theoretical vapor/liquid contacting stages employed in column 100 can vary widely, and will generally depend on the composition of the liquid feed to column 100, the degree of removal of impurities desired and other factors. Generally, however, from about 2 to 12 minimum theoretical stages, preferably from about 5 to 9 minimum theoretical stages are employed in column 100 above the liquid feed thereto, and from about 20 to 35 minimum theoretical stages, preferably from about 25 to 30 minimum theoretical stages, are employed below the liquid feed to column 100.

In FIG. 2 there is illustrated a second embodiment of the process of the present invention in which vicinal glycol esters are recovered from a liquid stream containing vicinal glycol esters, ester precursors, (including olefin carboxylic acid and catalyst), organo-halogen compound impurities, and non-halogenated by-products (including water), which stream is produced by an oxygen-based olefin oxidation process in which oxidation reactor 10 (operating, e.g., at a temperature from about 50° to 180° C. and a pressure of from about 50 to 1,000 psig) is fed an oxygen-containing gas (e.g., air) via conduit 14, the selected olefin (e.g., ethylene) via conduit 16, a carboxylic acid (e.g., acetic acid) via conduit 12, and a catalyst system (e.g., a mixture of a variable valent cation (such as any of those used in the processes of U.S. Pat. No. 3,689,535, Canadian Pat. No. 888,749 and the like) and a halogen-containing compound such as hydrogen bromide) via conduit 18. Vapors are withdrawn from reactor 10 via conduit 20 and may be recycled to reactor 10. A liquid stream comprising the impure vicinal glycol ester liquid to be treated by the process of the present invention is withdrawn from reactor 10 via conduit 34 and, after passing through pressure reducing valve 35, is passed as feed to the lower portion of first distillation column 40 (i.e., the "crude column"). The composition of the impure vicinal glycol ester liquid passed to crude column 40 may also vary widely, but (as when derived from an oxygen-based olefin-oxidation process) will generally comprise from about 10 to 80 weight percent, usually from about 15 to 70 weight percent, vicinal glycol esters; up to about 60 weight percent, usually from about 5 to 50 weight percent, carboxylic acid; up to about 10 weight percent, usually from about 0.01 to 50 weight percent, catalyst; up to about 5 weight percent, usually from about 0.01 to 1.0 weight percent, other ester precursors; up to about 10 weight percent, usually from about 0.2 to 8 weight percent, water; from about 5 to 20 weight percent, usually from about 7 to 16 weight percent, other non-halogenated by-products; and from about 0.1 to 50 weight percent, usually from about 10 to 20 weight percent, organo-halogen compound impurities.

Crude column 40 is operated under conditions of temperature and pressure such that upon introduction into lower portion 41 of column 40, at least a portion of the impure ester liquid vaporizes therein. Liquid is withdrawn via conduit 50 from the lower portion of zone 41 and comprises non-volatile components of the impure ester liquid such as non-volatile catalyst, together with sufficient vicinal glycol esters, halogenated and non-halogenated by-products, and ester precursors to provide ease of handling of the non-volatiles thereby withdrawn. The withdrawn bottoms can be recycled via conduit 56 as first bottoms product to reactor 10, with the addition of make-up acid, catalyst, etc., and with optional purging of a portion to prevent buildup of undesired heavy impurities in the system. A portion of the bottoms is passed via conduit 54 to reboiler 52 (which preferably comprises a oncethrough forced circulation, suppressed vaporization type) wherein the bottoms so recycled are heated without substantial vaporization of the recycled liquid, to minimize deposition of any non-volatiles contained therein on the surfaces of any process equipment. The heated liquid passing from reboiler 52 is then recycled via conduit 54 to lower portion 41 of crude column 40 to provide heat necessary to maintain the temperature selected for use in crude column 40. The heated recycled fluid, then at least partially vaporizes on passing into zone 41.

Vapors 45 (i.e., the vaporized portion of the impure ester liquid introduced via conduit 34 and the vaporized portion of the recycled heated fluid introduced via conduit 54) comprising vicinal glycol esters, volatile ester precursors, non-halogenated by-products and organo-halogen compound impurities are formed and pass upwardly through one or more trap-out trays 44 (e.g., chimney or trap-out trays of the type indicated in *Hydrocarbon Processing*, vol. 47, No. 7, pp. 119–120 (July 1968) and *Chemical Engineering Progress*, vol 65, No. 3, pp. 46–51 (March 1969)) into upper portion 43 of column 40 wherein the upwardly flowing vapors are contacted in countercurrent fashion with downwardly flowing liquid introduced to the upper portion of zone 43 via conduit 66. Vapors are withdrawn from zone 43 via conduit 42 and are passed to condenser 58. The condensate so produced, together with uncondensed vapors, are passed via conduit 60 to separator 62 from which the uncondensed vapors, comprising fixed gases ($CO$, $CO_2$, $N_2$, $C_2H_4$ and argon) carboxylic acid (e.g., acetic acid and/or formic acid), water, and other light materials are withdrawn via conduit 64. These vapors can be dehydrated to provide a purge of water formed during the oxidation and the remaining materials recovered for recycle to reactor 10. The water so removed can (after treatment for removal of any unsuitable impurities, if present) be advantageously used in hydrolysis of vicinal glycol esters produced by the process of the present invention to form the corresponding glycols. Condensate is withdrawn from separator 62 via conduit 66 and at least a portion thereof recycled to zone 43 as liquid reflux. The remaining condensate is withdrawn via conduit 67 and also dehydrated, if desired, to recover materials which can be recycled to reactor 10. The amount of liquid reflux to zone 43 may vary widely but is generally sufficient to provide a reflux ratio of from about 0.2:1 to 50:1 and preferably from about 0.4:1 to 20:1.

Liquids collecting on the upper portion of trap-out tray 44 are withdrawn from crude column 40 via conduit 48 and comprise vicinal glycol esters, organo-halogen compound impurities, and non-halogenated by-products. This withdrawn liquid is hereinafter referred to as the "crude ester mixture". Generally, at least about 90 percent of the water and generally at least about 80 percent of the carboxylic acid in the impure ester feed to crude column 40 are withdrawn as either uncondensed vapors and/or liquid from separator 62 via conduits 64 and 67, respectively. Thus, the crude ester mixture withdrawn from column 40 via conduit 48 will generally comprise up to about 15 weight percent, usually from about 5 to 10 weight percent, carboxylic acid; up to about 5 weight percent, usually from about 0.01 to 2 weight percent, other ester precursors; from about 10 to 80 weight percent, usually from about 50 to 70 weight percent, vicinal glycol esters; from about 2 to 30 weight percent, usually from about 10 to 20 weight percent, organo-halogen compound impurities; up to about 10 weight percent, usually from about 0.2 to 1 weight percent, water; and from about 2 to 60 weight percent, usually from about 5 to 50 weight percent, other non-halogenated by-products.

To minimize entrainment of non-volatiles and liquid droplets in vapor 45 passing upwardly through trap-out tray 44, crude column 40 is preferably provided with demister 46 which is positioned before trap-out tray 44 and above the inlet for the impure ester liquid feed, for removal of substantially all entrained material from vapor 45. Demister 46 may be suitably provided via conduit 49 with a portion of the crude ester mixture withdrawn from column 40 via conduit 48 in order to backwash demister 46 and thereby remove entrained material therefrom. Alternatively, trap-out tray 44 may be suitably provided with regularly spaced openings to permit some of the liquid collecting on trap-out tray 44 to flow downwardly over demister 46 to provide backwash fluid thereto.

The crude ester mixture is then passed as feed via conduit 48 to distillation column 70 (i.e., the "heavies column") as described above and the overhead product so produced is passed to distillation column 100 (i.e., the "ester column") for preparation of a bottoms product having substantially reduced concentrations of organohalogen compound impurities.

The conditions of temperature and pressure employed in crude column 40 can vary widely and will depend on a variety of factors such as the precise composition of the impure ester liquid fed thereto, the types of distillation apparatus employed, and other factors. However, to avoid undesired oxidation of the impure ester liquid and the attendent deposition of carbonized matter and solids on equipment and the pluggage difficulties resulting therefrom, it has been found necessary to employ a bottoms temperature in column 40 of not greater than about 190° C., and preferably from about 155° to 175° C. Thus, surface temperatures in reboiler 52 are preferably not greater than about 200° C. The quantity of the impure ester liquid introduced via conduit 34 to zone 41 which is vaporized therein can vary widely, generally being determined only by the amount of liquid desired to provide sufficient fluidity for handling of the bottoms withdrawn via conduit 50 and to provide sufficient liquid through reboiler 52 to satisfy the heat requirements of crude column 40. Generally, no more than about 25 percent, and preferably no more than about 16 percent, of the impure ester liquid introduced via conduit 34 is withdrawn as net bottoms via conduit 56. The pressure within crude column 40 can also vary widely, but will generally be at least 100 psi, and preferably at least about 300 psi, lower than the pressure selected for use in reactor 10.

The number of theoretical vapor/liquid contacting stages employed in zone 43 can vary widely, and will generally depend on such factors as the composition of the flashed ester feed, the degree of removal of vicinal glycol esters desired from vapors 45 and a variety of other factors. Generally, however, from about 5 to 15 minimum theoretical stages, and preferably from about 8 to 12 minimum theoretical stages, are employed in crude column 40 above trap-out tray 44, (i.e., in zone 43). While zone 43 can be provided with stripping trays such as sieve, disc, donut or valve trays, they are not necessary. Zone 41 will generally employ at least about 1 theoretical vapor/liquid contacting stages.

While not shown, it will be appreciated that crude column 40 can be provided with a conventional level control device (not shown) to sense the level of liquid collected on trap-out tray 44 and to control the amount of liquid withdrawn as crude ester mixture via conduit 48 by a suitably disposed valve (not shown) in conduit 48 and thereby prevent overflow of liquid through trap-out tray 44 into zone 41.

Since the impure vicinal glycol ester liquid withdrawn from reactor 10 generally contains dissolved therein components (hereinafter termed "normally gaseous compounds") which are gases at conditions of room temperature (25° C.) and atmospheric pressure, such as unreacted olefin (e.g., ethylene), fixed gases (e.g., oxygen and inert gases), and halogenated and non-halogenated oxidation by-products (e.g., carbon dioxide, carbon monoxide and vinyl bromide), impure ester liquid withdrawn from reactor 10 can be passed via conduit 28 to a flash zone, illustrated at 30 in the embodiment of FIG. 2, for removal of at least a portion of the normally-gaseous components from the impure ester liquid before passing the liquid to crude column 40 via conduits 26 and 34 for further treatment of the liquid for vicinal glycol ester recovery in accordance with this invention. Vapors produced in flash zone 30 may be withdrawn via conduit 32, and where desired, treated for recovery of unreacted olefin and any vicinal glycol ester also vaporized, which recovered material may then be recycled to reactor 10, or the vapors can be simply compressed and recycled to reactor 10.

The impure ester liquid may be flashed either isothermally or adiabatically, the latter being the preferred method and the method illustrated in FIG. 2. The conditions of temperature and pressure of adiabatic flash zone 30 will vary depending on the precise composition of the impure vicinal ester feed to flash zone 30, the amount of the normally-gaseous compounds sought to be removed therein, and a variety of other factors, and may be easily ascertained by the skilled practitioner. Thus, where adiabatic flashing is employed, flash zone 30 will be maintained at a lower pressure than is employed in oxidation reactor 10, generally at a pressure of at least 100 psi and more usually 300 psi, lower than is employed in oxidation reactor 10, and at a temperature of about 100° to 170° C., usually from about 120° to about 150° C. The impure ester liquid is preferably flashed under conditions sufficient to remove therefrom a majority (i.e., at least 50 weight percent), and most preferably at least about 90 weight percent, of the normally-gaseous compounds in the impure ester liquid withdrawn from the oxidation reactor.

Of course, it will be appreciated that the use of such a flash step to remove normally gaseous compounds from the impure vicinal glycol ester liquid is not critical to the process of the present invention, but rather, serves to reduce the size of a subsequent apparatus in the processing of the ester liquid to recover vicinal glycol esters therefrom in accordance with the process of this invention.

It will also be understood that one or more flash zones 30, one or more crude distillation columns 40, one or more heavies columns 70 and one or more ester columns 100 can be employed, in series or in parallel, the use of multiple flash zones, crude columns, and the like being dictated only by economics.

Figure 3:
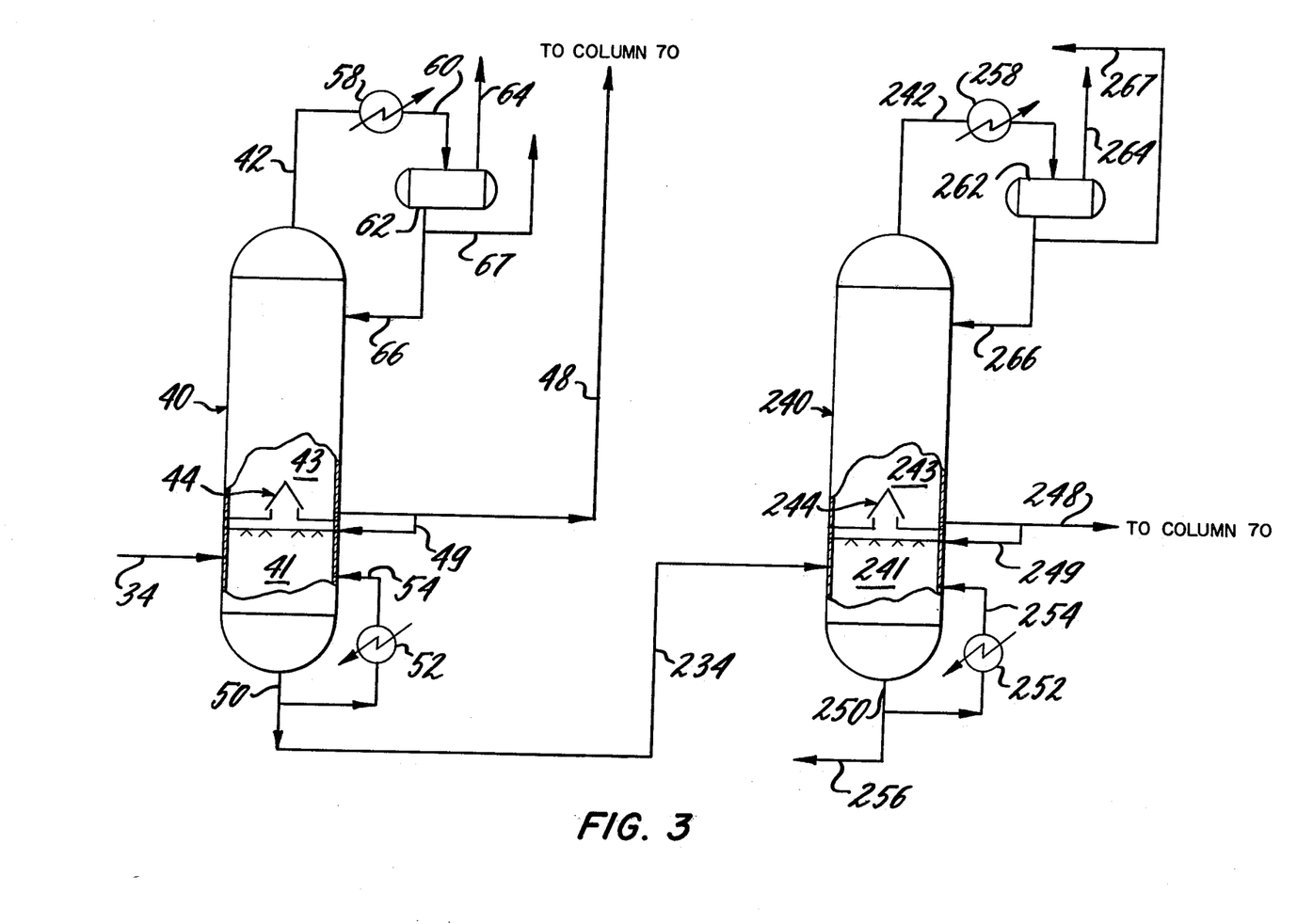
FIG. 3 is a diagrammatic illustration of yet another embodiment of the process of the present invention.

Thus, there is illustrated in FIG. 3 a further embodiment of the process of this invention in which the portion of the liquid bottoms product which is withdrawn from column 40 via conduit 50 and which is not recycled to the column via reboilers 52 and 54, is passed via conduit 234 to second crude distillation column 240 which, in the embodiment illustrated, is configured similarly to column 40 previously discussed, except that the numerals employed for column 40, its conduits, reboilers, and associated zones and equipment, are each preceded by the numeral "2". Thus, there is produced a net bottoms which may be withdrawn via conduit 256 for recycle, as described previously, to reactor 10, and a side product stream is withdrawn via conduit 248 which may be passed to column 70, as described previously, for recovery of the desired vicinal glycol esters having substantially reduced organo-halogen compound impurities. Of course, it would be appreciated that the compositions of liquid streams in conduits 48 and 248 will differ in the proportions of vicinal glycol ester, ester precursor, non-halogenated and organo-halogen compounds contained therein, and that such compositional differences may make desirable an introduction of each stream into column 70 at different feed points in the column, a determination which is dictated solely by economics and can be determined easily by one having ordinary skill in the art.

Figure 4:
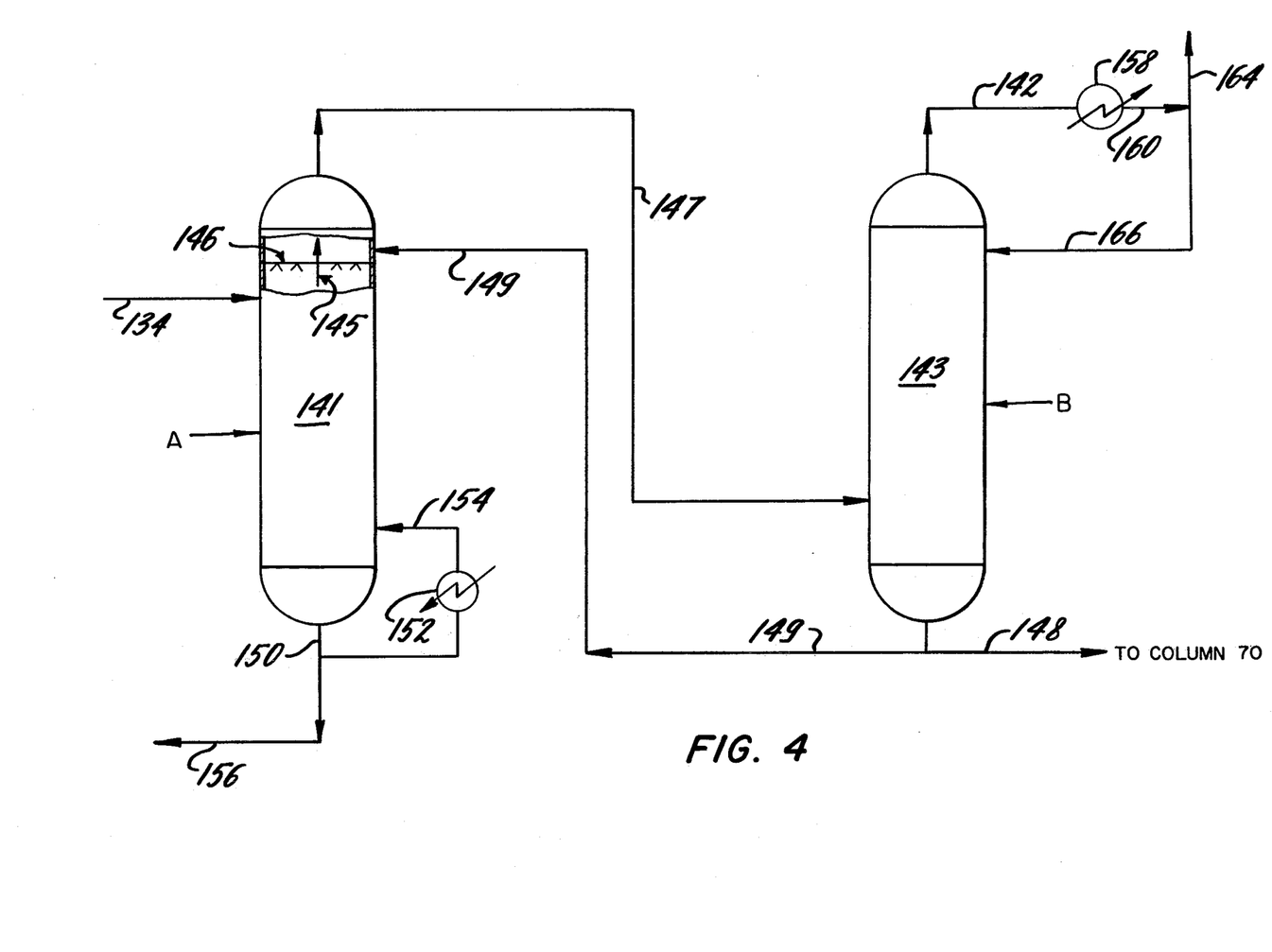
FIG. 4 is a diagrammatic illustration of still a further embodiment of the process of the present invention in which the distillations performed in column 40 of FIG. 2 are effected in separate distillation columns A and B.

Moreover, from the foregoing it would be obvious that while crude column 40 is illustrated in FIG. 2 as having two gas/liquid contacting zones (i.e., lower zone 41 and upper zone 43) disposed therein, each such zone can comprise a separate vessel, as is shown in FIG. 4 (wherein identifying numerals identical to those used in FIG. 2 are employed for common parts except that the numerals are preceded by "1"). In the embodiment of FIG. 4, therefore, impure vicinal glycol ester liquid is passed via conduit 134 to column A in which is disposed distillation zone 141 for formation of vapors 145 which pass upwardly through demister 146 and for formation of an overhead product withdrawn via conduit 147. A liquid bottoms product is withdrawn from column A via conduit 150, with a portion thereof being recycled via reboilers 152 and conduit 154 to column A to provide the heat necessary for operation of the column, and the remainder of such withdrawn liquid bottoms being removed via conduit 156, for optional recycle to reactor 10.

The overhead product, comprising vapors, withdrawn via conduit 147 from column A is passed to the lower portion of column B into distillation zone 143, wherein such vapors are contacted with downwardly flowing liquid introduced to the upper portion of column B via conduit 166. An overhead product is formed which is withdrawn from Column B via conduit 142 and condensed in condenser 158, from which condensate is withdrawn via conduit 160 and either recycled via conduit 164, as described previously, or passed as liquid reflux to column B via conduit 166. A liquid bottoms product is withdrawn via conduit 148 and can be passed to column 70 as described previously for recovery of desired vicinal glycol esters having substantially reduced concentrations of organo-halogen compound impurities. A portion of the bottoms product can be passed via conduit 149 to the upper portion of column A to provide the liquid wash necessary for operation of demister 146. Of course, in the event that insufficient heat is provided by the vapors contained in conduit 147 for operation of column B, a portion of the bottoms product withdrawn from the bottom of column B can be recycled thereto via a suitable reboiler (not shown) to provide added heat to the zone 143.

While the embodiments of FIGS. 1 through 4 illustrate the use of external reboilers in combination with the various distillation columns, it will be appreciated that conventional heat exchangers can be provided to preheat the feeds to the distillation columns, and that heating elements internal to the distillation columns can also be used.

By operating in the manner described above, significant reductions in impurities level in the impure vicinal glycol ester liquid are obtained. Under preferred conditions outlined above, it is readily possible to obtain removal of up to about 99.5 weight percent and more of the organo-halogen compound impurities from the impure vicinal glycol ester liquid, and to produce vicinal glycol esters containing concentrations of organo-halogen compound impurities on the order of about 10 to 20 ppm or lower (calculated as halide).

The vicinal glycol esters having substantially reduced concentration of organo-halogen compound impurities, which are produced by the process of the present invention, are suitable for use as such as solvents or plasticizers or they can readily be converted to free glycol by hydrolysis or, especially in the case of ethylene glycol diacetate, can be pyrolyzed to form vinyl acetate by known techniques.

The invention will be more fully understood by reference to the following specific examples, but it is to be understood that these examples are given solely for illustrative purposes and are not intended to be limitative of the invention. In the examples that follow throughout the specification, parts are by weight unless otherwise indicated.

EXAMPLE 1

An impure vicinal glycol ester liquid comprising 5.1 weight percent of water, 25.3 weight percent of a mixture of ethylene glycol monoacetate and ethylene diacetate, 0.5 weight percent of ethylene glycol bromoacetate and 0.5 weight percent of cerium bromide, together with acetic acid, non-halogenated by-products (such as diethylene glycol, triethylene glycol and mono- and di-acetic acid esters of the foregoing) and high-boiling organo-halogens (such as diethylene glycol dibromide, diethylene glycol bromoacetate, diethylene glycol bromohydrin, and ethylene glycol acetate bromoacetate), is isothermally flashed at a temperature of about 140° C. and at atmospheric pressure, thereby resulting in vaporization of about 70 weight percent of the liquid so treated. The remaining, unvaporized liquid is then passed as feed to a second flashing step, performed in a separate vessel, in which this liquid is flashed isothermally at a temperature of about 175° C. and at atmospheric pressure, thereby resulting in the vaporization of about 83% of the liquid passed to this second flashing step. The overheads from both flashing steps are collected and combined, and following condensation thereof are found to contain about 64.3 weight percent of water and acetic acid, 0.4 weight percent of ethylene glycol bromoacetate, and 32.9 weight percent of a mixture of ethylene glycol monoacetate and ethylene glycol diacetate, together with high-boiling organo-halogens and non-halogenated by-products, and is substantially free of catalyst.

The liquid so produced is fed at a rate of about 735 parts per hour to an Oldershaw distillation column (25.4 mm diameter; vacuum jacketed) which is provided with a 150 mm glass thermosiphon reboiler, and which has 60 plates above and 5 plates below the feed point. Employing a reflux ratio of 0.4, a head temperature of about 115° C., a reboiler temperature of about 161° C., a feed tray temperature of about 129° C. and an overhead pressure of about 760 mm Hg, overhead vapors are obtained which are found to contain 1.6 weight percent of a mixture of ethylene glycol monoacetate and diacetate, and 0.3 percent total organo-halogen compounds together with water, acetic acid and low-boiling non-halogenated by-products. There is also produced in this column a bottoms containing 71.4 weight percent of a mixture of ethylene glycol monoacetate and diacetate, 0.5 weight percent of ethylene glycol bromoacetate, and 22.2 percent of acetic acid and the high-boiling organo-halogens, together the the non-halogenated by-products.

These bottoms, comprising the crude ester mixture, are collected and then passed at a temperature of about 159° C. and at a rate of 330 parts per hour to a second vacuum jacketed Oldershaw distillation column having forty 24.5 mm diameter plates and ten 50.8 mm diameter plates above the feed and fifteen 50.8 mm diameter plates below the feed. The column is provided with a 150 milliliter glass thermosiphon reboiler. Employing a reflux ratio of 2, a head temperature of 174° C., a reboiler temperature of 200° C., a feed tray temperature of about 190° C., and an overhead pressure of about 760 mmHg, overhead vapors are obtained which are found to contain 72.6 weight percent ethylene glycol monoacetate and diacetate, 24.6 weight percent acetic acid, and 0.5 weight percent ethylene glycol bromoacetate together with low-boiling non-halogenated by-products. Bottoms from this column are obtained which are found to contain 60.6 weight percent of a mixture of ethylene glycol monoacetate and diacetate, and 0.4 weight percent ethylene glycol bromoacetate together with high-boiling organo-halogens and high-boiling non-halogenated by-products. These overhead vapors are condensed and the portion of the condensate not returned as reflux is passed as feed at a rate of about 297 parts per hour and at a liquid temperature of about 158° C. to a third distillation column (the "ester column") comprising a one-inch diameter vacuum jacketed Oldershaw column having twenty plates above and fifty plates below the feed point, and provided with 150 milliliter glass thermosiphon reboiler. Operating at a reflux ratio of 2.5, a head temperature of 133° C., a reboiler temperature of 192° C., a feed tray temperature of 184° C. and an overhead pressure of about 760 mmHg, overheads are obtained which are found to comprise 1.5 weight percent ethylene glycol bromoacetate, 17 weight percent of a mixture of ethylene glycol monoacetate and diacetate, and 74.6 weight percent acetic acid together with other low-boiling materials, such as the low-boiling organo-halogens and low-boiling non-halogenated by-products. Bottoms are withdrawn at a rate of about 200 parts per hour from the ester column and are found to contain 99.98 weight percent of a mixture of ethylene glycol monoacetate and diacetate and 0.02 weight percent of ethylene glycol bromoacetate. Thus, a product stream is obtained which contains a concentration of vicinal glycol esters which is about 400 percent greater than that of the impure vicinal glycol ester liquid which is treated, but which contains organo-halogen impurities in a concentration which is over 2,500 percent *lower* than that of the impure liquid which is so treated.

EXAMPLE 2

The procedure of Example 1 is repeated except that the reflux ratio of the ester column is increased to 5. The ethylene glycol bromoacete content of the bottoms obtained from the ester column is found to decrease to 0.002 weight percent, thereby providing a vicinal glycol ester liquid containing 99.998 weight percent of a mixture of ethylene glycol monoacetate and diacetate.

In a separate run, the procedure of Example 1 is repeated except that the reflux ratio employed in the ester column is decreased to about 1.75. The bottoms produced in the ester column are then found to contain ethylene glycol bromoacetate in a concentration of about 0.07 weight percent, thereby providing a vicinal glycol ester liquid containing 99.93 weight percent of a mixture of ethylene glycol monoacetate and diacetate.

EXAMPLE 3 [FOR COMPARISON]

In order to show the surprising effect which operation according to the process illustrated in Example 1 has upon the concentration of low-boiling organo-halogen compound impurities in a vicinal glycol ester liquid obtained by a reversed distillation sequence (in which the impure liquid is first distilled for removal of the low-boiling impurities and the bottoms thereby obtained subsequently distilled for removal of the desired ester liquid as overheads).

The liquid produced following condensation of overheads from the two flashing steps of Example 1 is fed at a rate of about 735 parts per hour to a 50.8 mm diameter vacuum jacketed Oldershaw distillation column which is provided with 20 plates above the feed, thirty plates below the feed and a 150 milliliter glass thermosiphon reboiler. Employing a reflux ratio of 0.8, a head temperature of about 150° C., a reboiler temperature of about 194° C., a feed tray temperature of about 180° C. and an overhead pressure of about 760 mmHg, overhead vapors are obtained which are found to contain 4.6 weight percent of a mixture of ethylene glycol monoacetate and diacetate, and 2.2 weight percent ethylene glycol bromoacetate together with water and acetic acid. Bottoms are formed which are found to contain 0.4 weight percent ethylene glycol bromoacetate, and 94.4 weight percent of a mixture of ethylene glycol monoacetate and diacetate together with high-boiling ogano-halogens and high-boiling non-halogenated by-products.

The bottoms thereby obtained are passed at a temperature of about 194° C. and at a rate of about 232 parts per hour to a vacuum jacketed Oldershaw distillation column having thirty-five 25.4 mm diameter plates, of which thirty plates are above the feed point, and provided with a 150 milliliter glass thermosiphon reboiler. Employing a reflux ratio of 2.2, a head temperature of about 190° C., a reboiler temperature of about 200° C. and an overhead pressure of about 760 mmHg, overhead vapors are obtained which contain 99.6 weight percent of a mixture of ethylene glycol monoacetate and diacetate and 0.4 weight percent of ethylene glycol monoacetate, and bottoms are obtained which are found to contain 60.6 weight percent of a mixture of ethylene glycol monoacetate and diacetate together with the high-boiling materials.

Therefore, the distillation sequence employed in this example results in a vicinal glycol ester liquid containing 0.4 weight percent of organo-halogen impurities.

In separate runs, the reflux ratio of the first distillation column is increased to 1.2 and subsequently in a separate run to 1.5. However, the concentration of ethylene glycol bromoacetate in the bottoms from this first column, as well as the concentration of this impurity in the overheads from the second column, is found to be substantially unaltered. In yet another separate run, the number of distillation plates below the feed in the first distillation column is increased to 50 and a reflux ratio of 0.8 is employed. However, the concentration of ethylene glycol bromoacetate in the bottoms thereby obtained from the first distillation column is found to remain about 0.4 weight percent.

Therefore, altering the reflux ratios and the number of distillation plates in the first distillation column, wherein separation of low-boiling organo-halogens as overhead is desired, is found not to result in a bottoms from this column which contains significantly increased concentration of the undesired low-boiling organo-halogens, so that when such bottoms are passed through the second distillation column, the low-boiling organo-halogens present in the bottoms passed to the overhead obtained in the second distillation column and thereby contaminates the desired vicinal gycol esters contained in the vapor to an unacceptable degree.

EXAMPLE 4

In order to show the formation of low-boiling organo-halogen compounds from high-boiling organo-halogen compounds, about 136 parts of the bottoms product obtained from the first distillation column of Example 3, which is analyzed to contain about 300 ppm of ethylene glycol bromoacetate, is charged to a 250 milliliter flask. The liquid is heated to a temperature of 194° C. and atmospheric pressure and is held at total reflux for a period of 58 hours. Samples are taken at different times during this operation and analyzed for ethylene glycol bromoacetate content, thereby yielding the data set forth in Table 1 below:

TABLE 1

| TIME (Hours) | EGBA *Content (ppm) |
|---|---|
| 0 | 300 |
| 8 | 5000 |
| 13 | 8000 |
| 23 | 10000 |
| 58 | 14000 |

*Ethylene glycol bromoacetate

Thus, it is shown that the high-boiling organo-halogen compounds generate additional low-boiling organo-halogen compounds under conditions of distillation in the second distillation column of Example 3.

EXAMPLE 5

In order to show the ability of facile separation of low-boiling organo-halogens from a liquid containing reduced quantities of high-boiling organo-halogens, an impure vicinal glycol ester liquid containing 91 weight percent of a mixture of ethylene glycol monoacetate and diacetate, 0.025 weight percent of ethylene glycol bromoacetate and an unknown quantity of high-boiling organo-halogens and high-boiling non-halogenated by-products is fed at a rate of 250 parts per hour to a 50.8 mm diameter vacuum jacketed Oldershaw column arranged as detailed for the second distillation column of Example 3. Employing a reflux ratio of 2.0, the overhead product which is obtained is found to contain 98 weight percent of a mixture of ethylene glycol monoacetate and diacetate and 0.8 weight percent ethylene glycol bromoacetate. As in Example 4, therefore, the high-boiling organo-halogen compounds in the liquids passed to this distillation column are generating low-boiling organo-halogen compounds during distillation.

The overhead product thus obtained is passed to a 3-necked 12-liter flask to which is attached a twenty plate 50.8 mm diameter vacuum jacketed Oldershaw column, and the liquid so charged is batch distilled employing a reflux ratio of 10, until 40 weight percent of the initial charge is removed as overhead. During distillation the pot temperature is 132° C. and the overhead temperature is 127° C. At the completion of the distillation, the liquid remaining in the flask is analyzed and is found to contain 40 ppm ethylene glycol bromoacetate, thereby indicating that no additional low-boiling organo-halogens are formed during distillation in the absence of the high-boiling organo-halogens.

It will be obvious that various changes and modifications may be made without departing from the invention and it is intended, therefore, that all matter contained in the foregoing description shall be interpreted as illustrative only and not limitative of the invention.

I claim:

1. A process for producing vicinal glycol esters having reduced concentrations of organo-halogen compound impurities from impure vicinal glycol ester liquids containing organo-halogen compound impurities having normal boiling points higher and lower than the vicinal glycol esters which comprises distilling the impure liquid in a first distillation zone to form a first bottoms product comprising higher-boiling organo-halogens and a first overhead product comprising vicinal glycol esters and lower-boiling organo-halogens, and distilling at least a portion of the first overhead product in a second distillation zone to form a second overhead product comprising lower-boiling organo-halogens and a second bottoms product comprising vicinal glycol esters containing the reduced concentrations of organo-halogen compound impurities.

2. The process according to claim 1 wherein the first distillation zone employs at least from about 5 to 15 theoretical vapor/liquid contacting stages in said zone above the feed of said impure liquid thereto and at least about 1 to 10 theoretical vapor/liquid contacting stages below the feed of said impure liquid thereto.

3. The process according to claim 1 wherein a portion of the first overhead product is recycled as reflux to the first distillation zone, employing a liquid reflux ratio of at least from about 0.01:1 to 10:1.

4. The process according to claim 1 wherein the first overhead product contains not greater than about 1 weight percent of said higher-boiling organo-halogen compound impurities passed to the first distillation zone with the impure liquid.

5. The process according to claim 1 wherein the second distillation zone is provided with at least from about 2 to 12 theoretical vapor/liquid contacting stages above the feed of the first overhead product thereto, and at least from about 20 to 35 theoretical vapor/liquid contacting stages below the feed of the first overhead product thereto.

6. The process according to claim 1 wherein the second overhead product is recycled as reflux to the second distillation zone in an amount sufficient to provide a reflux ratio of at least from about 0.1:1 to 10:1.

7. The process according to claim 1 wherein the second bottoms product contains less than about 0.2 weight percent of organo-halogen compound impurities.

8. In the production of vicinal glycol esters by an oxygen-based olefin-oxidation process in which olefin is reacted with molecular oxygen and carboxylic acid in the presence of metallic catalyst and halogen-containing compounds to produce an impure vicinal glycol ester liquid comprising vicinal glycol esters, organo-halogen compound impurities having normal boiling points higher and lower than the vicinal glycol esters, water, carboxylic acid, metallic catalyst, and non-halogenated by-products having normal boiling points higher and lower than the vicinal glycol esters, and the impure vicinal glycol ester liquid is treated for recovery of the vicinal glycol esters, the improvement which comprises recovering vicinal glycol esters having reduced concentrations of said organo-halogen compound impurities from said impure liquid by a process comprising the steps of:

(a) distilling said impure liquid in a first distillation zone to form (i) a first overhead product comprising vicinal glycol esters, organo-halogen compound impurities, water, carboxylic acid and non-halogenated by-products, and (ii) a first bottoms product containing metallic catalyst;

(b) distilling the first overhead product in a second distillation zone to form (i) a second bottoms product comprising vicinal glycol esters, organo-halogen compound impurities and non-halogenated by-products, and (ii) a second overhead product containing water and carboxylic acid;

(c) distilling the second bottoms product in a third distillation zone to form (i) a third overhead product comprising vicinal glycol ester, lower-boiling organo-halogens, and lower-boiling non-halogenated by-products and (ii) a third bottoms product comprising higher-boiling organo-halogens and higher-boiling non-halogenated by-products;

(d) distilling the third overhead product in a fourth distillation zone to form (i) a fourth overhead product comprising lower-boiling organo-halogens and lower-boiling non-halogenated by-products and (ii) a fourth bottoms product comprising the desired vicinal glycol esters having substantially reduced concentration of said organo-halogen compound impurities; and (e) withdrawing said fourth bottoms product from the fourth distillation zone as product.

9. The process according to claim 8 wherein the first distillation zone employs at least 1 theoretical vapor/liquid contacting stage.

10. The process according to claim 8 wherein the second distillation zone employs at least from about 5 to 15 theoretical vapor/liquid contacting stages.

11. The process according to claim 8 wherein the third distillation zone employs at least from about 5 to 15 theoretical vapor/liquid contacting stages in said zone above the feed of said second bottoms product thereto and from at least about 1 to 10 theoretical vapor/liquid contacting stages below the feed of said second bottoms product thereto.

12. The process according to claim 8 wherein a portion of the third overhead product is recycled as reflux to the third distillation zone, employing a liquid reflux ratio of at least from about 0.01:1 to 10:1.

13. The process according to claim 8 wherein the third overhead product contains not greater than about 1 weight percent of said higher-boiling organo-halogen compound impurities passed to the third distillation zone with said second bottoms product.

14. The process according to claim 8 wherein the fourth distillation zone is provided with at least from about 2 to 12 theoretical vapor/liquid contacting stages above the feed of the third overhead product thereto, and at least from about 20 to 35 theoretical vapor/liquid contacting stages below the feed of the third overhead product thereto.

15. The process according to claim 8 wherein the fourth overhead product is recycled as reflux to the fourth distillation zone in an amount sufficient to provide a reflux ratio of from about 0.1:1 to 10:1.

16. The process according to claim 8 wherein the fourth bottoms product contains less than about 0.2 weight percent of organo-halogen compound impurities.

* * * * *